United States Patent
Borodulin et al.

Patent Number: 5,817,127
Date of Patent: Oct. 6, 1998

[54] COMBINED DILATOR-URETHROTOME

[76] Inventors: German Borodulin, 583-46th Ave., San Francisco, Calif. 94121; Alexander Shkolnik, 485 Dartmouth Ave., San Carlos, Calif. 94070; Maxim Persidsky, 35 Temescal, San Francisco, Calif. 94118

[21] Appl. No.: 869,291

[22] Filed: Jun. 4, 1997

[51] Int. Cl.⁶ .......................... A61M 29/00; A61B 17/32; A61B 1/22; A61B 1/30

[52] U.S. Cl. .......................... 606/198; 606/191; 606/167; 600/201; 600/222

[58] Field of Search .................. 606/1, 167, 170, 606/171, 190–200; 600/201, 204, 205, 210, 214, 215, 220, 221, 222

[56] References Cited

U.S. PATENT DOCUMENTS

| | | | |
|---|---|---|---|
| 1,624,716 | 4/1927 | Cerbo | 600/184 |
| 4,690,132 | 9/1987 | Bayer et al. | 600/184 |
| 5,345,927 | 9/1994 | Bonutti | 600/208 |
| 5,667,520 | 9/1997 | Bonutti | 606/190 |

*Primary Examiner*—Glenn K. Dawson

[57] ABSTRACT

A combined mechanical dilator-urethrotome comprising a radially-expandable probe (12) consisting of two rods (16 and 18) of a semicircular cross-section which form a complete circle in a closed state of the probe. One of the rods (16) has a core (32) rigidly attached thereto at the proximal end of this rod and arranged at an angle to the direction of the probe. The second rod (18) has a post portion (52) at the proximal end. The post portion (52) has a central opening (51), and the aforementioned core (32) is slidingly inserted into the central opening (51). The end of the core that projects beyond the limits of the post is connected to a handle (14) that can rotate with respect to the core (32) and has a thread engageable with the mating thread on the post. As a result, rotation of the handle causes screwing or unscrewing of the thread of the handle onto or from the thread of the post. Displacement of the handle (14) with respect to the core (32) causes expansion or contraction of the probe. Longitudinal slots are cut in both rods for insertion of a knife (42) that allows incision of constructions that may occur in the urethra. The same slots can be used for attachment of diameter-expanding pads (84) that increase the total outside diameter of the probe and make it suitable for use in a very wide rage of dilation diameters. The instrument can be used as a universal mechanical dilator and a urethrotome.

10 Claims, 2 Drawing Sheets

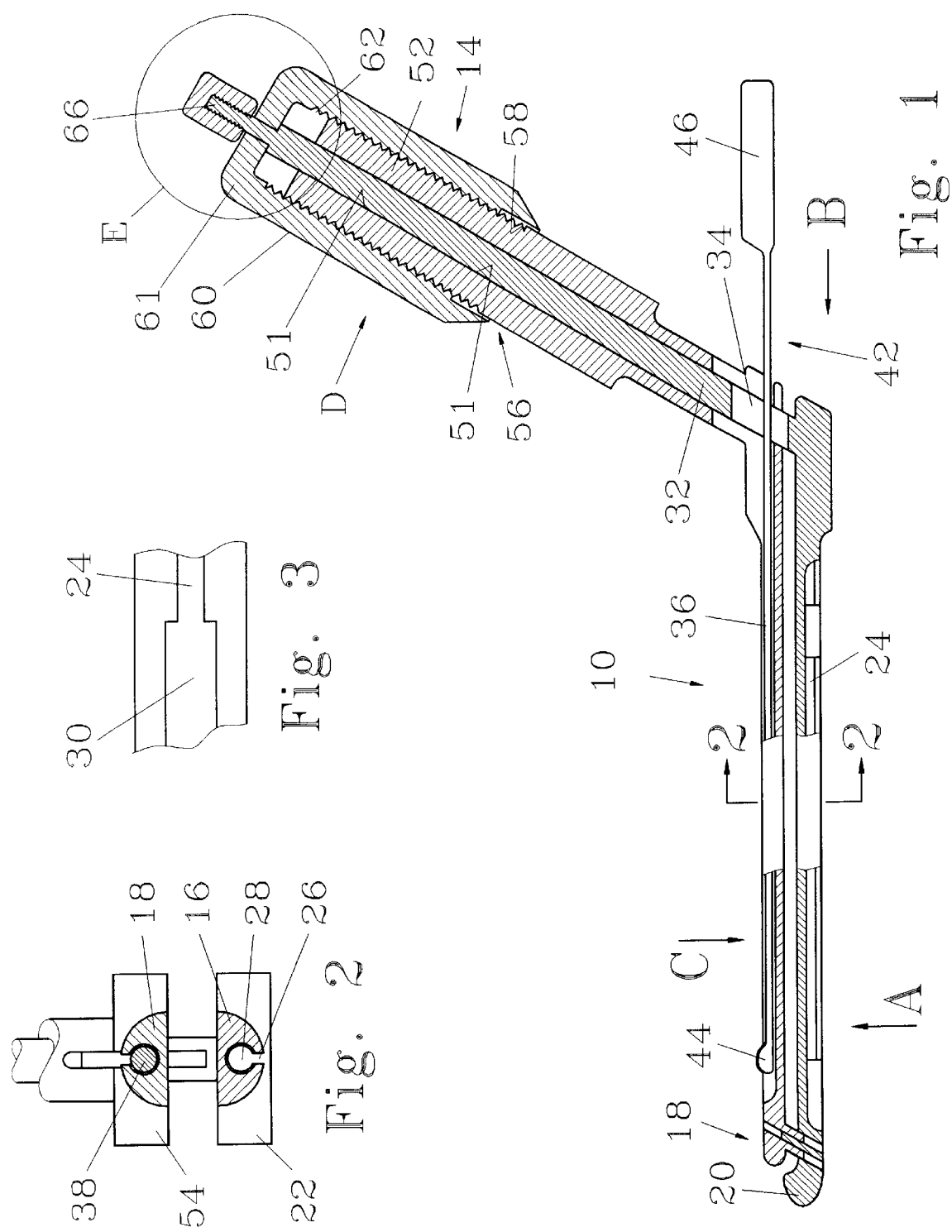

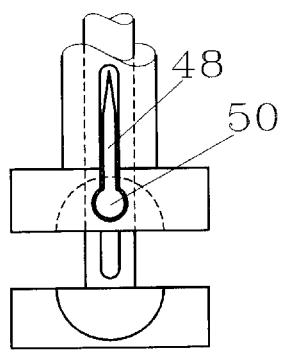
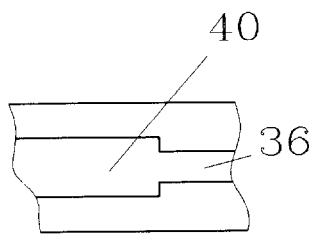
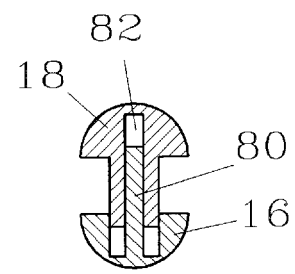
Fig. 4  Fig. 5  Fig. 8
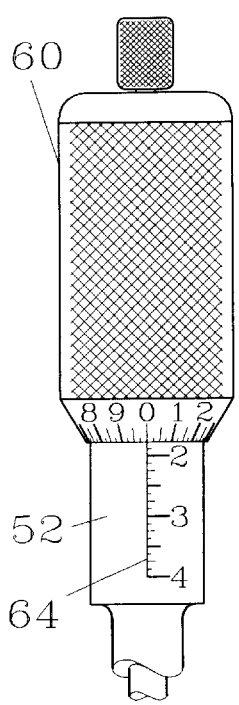
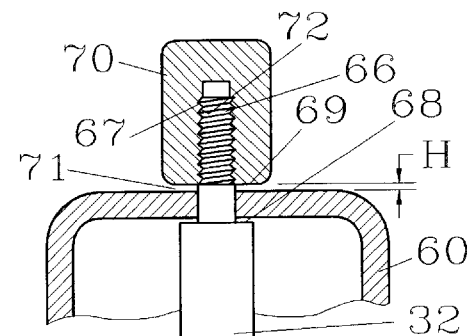
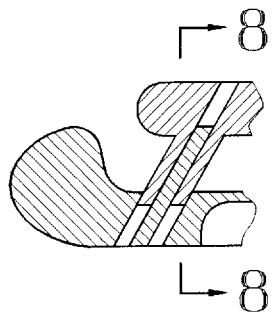
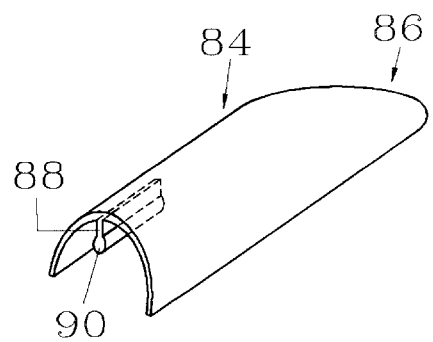
Fig. 6  Fig. 7  Fig. 9  Fig. 10

COMBINED DILATOR-URETHROTOME

FIELD OF INVENTION

The present invention relates to medical instruments, particularly to a urological instrument that combines functions of a mechanical urethral dilator with functions of a urethrotome.

BACKGROUND OF THE INVENTION

Urethral dilation is one of the most frequently used procedures in urological practice. For some patients, dilation of the urethra is the only procedure required for treatment (e.g., in the case of urethral strictures), whereas for others dilation is only a part of the treatment procedure (e.g., in the case of different transurethral operations).

To perform a dilation, a doctor is usually uses a set of straight urethral probes with gradually increasing diameters. It is understood that each insertion may increase probability of serious complications. Therefore the applicants have developed a series of mechanically expandable dilators which replace each a set of straight urethral probes or bougies.

One such dilator is disclosed in U.S. Pat. No. 4,911,149 to Borodulin, et al. issued in 1990. It comprises a probe shaped for insertion into urethra and consisting of two rods semicircular in a cross-section so that in a closed state of the probe they form in a cross section of the probe a complete circle. For dilation of the urethra to a required diameter the rods are moved apart from each other by a camming action of a wedge that is formed on a core element. The core element is placed between the rods and extends in the longitudinal direction of the probe. The core element is connected to a threaded handle that is threaded onto the proximal end of the probe so that rotation of the handle causes axial displacement of the core element together with the wedging cams. As a result of the axial movement of the cams with respect to the rods, the probe is either expanded or contracted.

The use of the aforementioned single adjustable urethral dilator that covers a range of diameters is advantageous. However, the mechanical dilator described in the above patent has a configuration more suitable for dilation of the male urethra. Although the probe of a mechanically-expandable dilator can be expanded within a certain range, this range is limited by structural capabilities of the dilator. For example, one mechanical dilator may be expanded from 18 F size to 28 F size or from 24 F to 35 F. (Here F means a special measurement unit used in the urology for dimensions of catheters, probes, and cystoscopes. In fact, 1 mm is equal to 3 F.) In some cases the urethras have to be dilated wider than the physiological size. Therefore a urologist has to acquire a set of dilators, even though these are mechanically expandable instruments.

On the other hand, if stricture is present in the urethra which is subject to dilation, an incision of this stricture may be required. In this case, a separate special urological surgical instrument known as a urethrotome has to be used. For this purpose, the dilator has to be removed from the urethra and a urethrotome has to be inserted to perform the aforementioned incision. This is inconvenient and involves an additional risk of complications.

OBJECTS OF THE INVENTION

It is an object of the present invention to provide a universal dilator-urethrotome which is simple in construction, reliable in operation, inexpensive to manufacture, universal in its functions, can be used as a mechanical dilator that covers a very wide range of diameters, can be used as a surgical cutter for urethral incisions, and replaces a set of mechanically-expandable dilators due to the use of diameter-expanding replaceable pads.

These and other objects and features of the invention will become more apparent after consideration of the ensuing description with the accompanying drawings.

BRIEF DESCRIPTION OF THE DRAWINGS

FIG. 1 is a general longitudinal sectional view of a dilator-urethrotome of the present invention.

FIG. 2 is a sectional view along lines 2—2 of FIG. 1.

FIG. 3 is a fragmental view of the probe in the direction of arrow A.

FIG. 4 is a fragmental view of the dilator-urethrotome in the direction of arrow B.

FIG. 5 is a fragmental view of the probe in the direction of arrow C.

FIG. 6 is a view of the handle in the direction of arrow D of FIG. 1.

FIG. 7 is zone E of FIG. 1 shown on a larger scale.

FIG. 8 is an enlarged sectional view along lines 8—8 of FIG. 9.

FIG. 9 is a fragmental view of the distal end of the probe made in accordance with another embodiment of the invention.

FIG. 10 is a three-dimensional view of one of diameter-expansion pads used for expanding the diameter of the probe.

SUMMARY

A combined dilator-urethrotome in the form of a radially-expandable probe consisting of two rods of a semicircular cross-section which form a complete circle in a closed state of the probe. One of the rods has a core rigidly attached thereto at the proximal end of this rod and arranged at an angle to the direction of the probe. The second rod has a post portion at the proximal end. The post portion has a central opening, and the aforementioned core is slidingly inserted into the central opening. The end of the core that projects beyond the limits of the post is connected to a handle that can rotate with respect to the core and has a thread engageable with the mating thread on the post. As a result, rotation of the handle causes screwing or unscrewing of the thread of the handle onto or from the thread of the post. Displacement of the handle with respect to the core causes expansion or contraction of the probe. A longitudinal slot is cut in one of the rods for insertion of a knife that allows incision of constrictions that may occur in the urethra. The same slot together with the similar slot in the second rod can be used for attachment of diameter-expanding pads that increase the total outside diameter of the probe and makes it suitable for use in a very wide range of dilation diameters. The instrument can be used as a universal mechanical dilator and a urethral urethrotome.

DETAILED DESCRIPTION OF THE COMBINED DILATOR AND URETHROTOME

A combined dilator-urethrotome of the present invention is shown in FIG. 1, which is a general longitudinal sectional view of the instrument. As shown in this drawing, the dilator-urethrotome, which as a whole is designated by reference numeral 10, consists of two main parts, i.e., a radially-expandable probe 12 (hereinafter referred to as "probe") and a handle 14 which, for convenience of handling and for improving conditions of observation, is arranged at an angle to the longitudinal direction of probe 12. This angle may vary within the range of 90° to 175°.

Probe 12 consists of two rods 16 and 18. As can be seen in FIG. 2, which is a sectional view along lines 2—2 of FIG. 1, rods 16 and 18 (hatched portion in FIG. 2) each have a semicircular cross-section so that in a closed state of the probe they form a complete circle in a cross section of the probe (in FIGS. 1 and 2 probe 12 is shown in an expanded state, i.e., with rods 16 and 18 spread apart radially outwardly for dilation of the urethra (not shown). On its distal end rod 16 has a rounded nose portion 20 of a hemispherical configuration and on its proximal end it has a thickened portion 22 of a rectangular cross section (FIG. 2). Rod 16 has a longitudinal slot 24 that extends from rounded nose portion 20 to thickened portion 22. As can be seen from FIG. 2, in its cross section, slot 24 has two parts, i.e., a narrow guide portion 26 and a locking portion 28 of a profiled cross section. The purpose of slot 24 and portions 26 and 28 will be described later in connection with the description of expansion pads insertable into the slot 24.

As shown in FIG. 3 which is a fragmental view of probe 12 in the direction of arrow A, slot 24 has at its distal end a window 30 which is wider than the remaining portion of slot 24. On its proximal thickened portion 22 and on the side opposite to the location of slot 24, rod 16 has a core member 32 that extends upward in the longitudinal direction of handle 14 and thus is inclined to the longitudinal direction of probe 12 at the same angle as handle 14. Core member 32 is rigidly connected to rod 16 or made integrally therewith. As can be seen from FIG. 4, which is a fragmental view of the dilator-urethrotome in the direction of arrow B, core 32 has at its end connected to thickened portion 22 of rod 16 a through slot 34. This slot is aligned and connected with a longitudinal slot 36 cut in rod 18 to a portion of its thickness. As can be seen from FIG. 2, longitudinal slot 36 has the same length and cross-sectional configuration as aforementioned slot 24 of rod 16. In other words, it has a narrow guide portion (not shown) and a wider profiled locking portion 38 (FIG. 2). Similarly, as shown in FIG. 5 which is a fragmental view of probe 12 in the direction of arrow C, slot 36 has at its distal end a window 40 which is wider than the remaining portion of slot 36.

As shown in FIG. 1, a surgical knife 42 may be slidingly inserted into slot 36 of rod 18 for cutting strictures of the urethra, if necessary. Such strictures may be represented, e.g., by scar tissues or narrowing of the orificium of the urethra. Knife 42 has a cutting blade portion 44 on the distal end of the knife and a handle portion 46 at the proximal end of the knife. As can be seen from FIG. 4, in its cross section, knife 42 has a shape conforming to the cross-sectional configuration of slot 36. In other words, it has a narrow portion 48, which is guided in narrow guide portion of slot 36, and a wider portion 50. Knife 42 is insertable from the rear side of dilator-urethrotome 10 through aforementioned slot 34 (FIG. 4) and further into slot 36 of rod 18.

Core member 32 is slidingly inserted into a central or longitudinal opening 51 of a cylindrical post 52 that extends from a proximal thickened portion 54 (FIG. 2) of rod 18 at the same angle with respect to probe 12 as core member 32. Similar to portion 22, thickened portion .54 has a rectangular cross section. Cylindrical post 52 has a portion 56 of an enlarged diameter with an outer thread 58. A cup shaped handle portion 60 has a closed end 61 and an inner thread 62 which is screwed onto outer thread 58 of cylindrical post 52 so that as handle is rotated, it moves with respect to cylindrical post 52.

As shown in FIG. 6, which is a view of the handle in the direction of arrow D of FIG. 1, a scale 64 is formed on the surface of cylindrical post 52, so that the amount of displacement of cylindrical post 52 with respect to handle portion 60 can be measured by observing the position of the edge of handle portion 60 with respect to scale 64.

The end of core member 32 opposite to probe 12 has a portion 66 of a diameter smaller than the diameter of core member 32 so that a shoulder 68 is formed. As shown in FIG. 7, which is a zone E of FIG. 1 illustrated on a larger scale, portion 66 has a male thread 67, and a cap 70 having a female thread 72 in a blind hole is screwed onto male thread 67. Threads 67 and 70 have directions opposite to threads 58 and 62. When cap 70 is screwed onto male thread 67 to the end, its end surface 69 does not reach the rear surface 71 of closed end 61 of handle portion 60, so that a small gap H (FIG. 7) is left in order to ensure free rotation of handle portion 60 with respect to cap 70 and core member 32.

FIG. 8 is an enlarged sectional view along lines 8—8 of FIG. 9 which is a fragmental view of the distal end of probe 12 which has auxiliary guide means in the form of a projection 80 made on the flat surface of one of the rods and a slot 82 made on the mating surface of the other rod. As a result, the rods have constantly overlapped guides which are not disconnected even in the position of maximum dilation of the probe so that rods are always protected from being shifted in the direction perpendicular to the longitudinal direction of the probe. As can be seen from FIG. 9, overlapped guides 80 and 82 are inclined to the longitudinal axes of the probe and has the same angle of inclination as the angle formed by handle 14 to the longitudinal direction of probe 12. Provision of guide members such as projection 80 and slot 82 prevents rotation of rod 18 with respect to rod 16 around post 32. As knife 42 passes through slots 36 and 34 of both rod 36 and post 32, it acts as a key or as an additional means that prevents rotation of rod 18 around post 32 and hence relative to rod 16.

FIG. 10 illustrates a diameter-expansion pad 84 used for expanding the diameter of probe 12 without replacing a dilator designed for a predetermined range of dilation diameters by another instrument that covers diameters of another range. FIG. 10 is a three-dimensional view of one of the expansion pads. It can be seen that expansion pad 84 is tapered to the proximal end 86 in order to facilitate insertion of the probe with the expansion pads into the urethra. Expansion pad 84 has a semicylindrical outer surface that corresponds to the outer surface of an appropriate rod of the probe. On the inner side, pad 84 has a radial projection of the same cross-sectional configuration as knife 42 and slot 36, i.e., it has a narrow guide portion 88 that corresponds to guide portion 26 of slot 24 and a locking portion 90 of a larger cross section that corresponds to portion 28 of the slot.

It is understood that two such expansion pads are used, one for each rod 16 and 18. Since both pads are essentially identical in construction, only one of them is shown in FIG. 10.

Pad 84 is connected to a respective rod, e.g., to rod 16, by inserting its locking portion 90 into slot 24 via window 30 (or window 40 in the case of rod 18), and then the pad is shifted rearward toward the proximal end of the probe by guiding its radial projection along slot 24 until the inner surface of the pad at its tapered end 86 comes into engagement with rounded nose portion 20 at the distal end of rod 16. The second pad (not shown) is connected in the same manner, and in the finally connected position (not shown) both rods define new semicylindrical working surfaces of the respective rods that acquire lager diameters than the rods themselves.

It is preferable that all parts of dilator-urethrotome 10 be made of a medically-acceptable stainless steel. The instrument can be easily disassemble for sterilization purposes.

OPERATION

Prior to dilation of the urethra, rods 16 and 18 of probe 12 should be closed to reduce the probe to its minimal diameter, i.e., when in cross section both rods form a complete circle. After appropriate procedures such as gelation, probe 12 is inserted into the urethra, and then dilation is carried out by rotating handle 60 in such a direction that, due to engagement of inner thread 62 with outer thread 58 of cylindrical post 52, rod 18 which is made integrally with larger-diameter portion 56 of post 52 is raised up from rod 16, whereby probe 12 is expanded. The expansion is measured by observing the position of the edge of handle portion 60 with respect to scale 64.

Upon completion of the dilation, handle 60 is rotated in the opposite direction, so that probe 12 is constricted and can be easily removed from the urethra.

If the urethra has a narrowing which has to be cut after the insertion of the probe into the urethra, the cutting can be performed with the use of knife 42. For this purpose, knife 42 is inserted into slot 34 from the rear side of the probe and further into slot 36. Incision can be carried out by reciprocating knife 42 back and forth within slot 36 by holding the knife by its handle 46 and cutting the stricture by means of its blade portion 44. If deeper cut is needed, the probe is further expanded and the cutting procedure is repeated. In other words, the instrument may be used as a conventional urethrotome.

If necessary, blade portion 44 can be preliminarily inserted into slot 34 and only slightly into slot 36 for additionally securing rods 16 and 18 against rotation with respect to each other. It is understood that in this case the blade portion is kept in the part of the probe which is not inserted into the urethra.

If the diameter of the probe needs to be additionally expanded, knife 42 is removed (if it is still present in slot 36), and diameter-expanding pads 84 of the type shown in FIG. 10 are inserted into respective slots 36 and 24. For this purpose, a locking portion 90 of each pad is inserted into windows 30 and 40, respectively, and then each pad is shifted toward the proximal end of the probe till further movement of each pad becomes impossible due to contact of the inner surface of its tapered portion 86 with the distal end of the respective rod.

Thus, it has been shown that the invention provides a universal dilator-urethrotome which is simple in construction, reliable in operation, inexpensive to manufacture, universal in its functions, can be used as a dilator that covers a very wide range of diameters, can be used as a surgical cutter for urethral incisions, and replaces a set of mechanically-expandable dilators due to the use of diameter-expanding replaceable pads.

Although the invention has been shown and described with reference to specific structural embodiments, it is understood that these embodiments were given only as examples and that they do not limit the field of practical applications. Therefore any modifications and changes are possible without deviation from the scope of the attached patent claims. For example, the handle portion can be made of plastic. If necessary, all parts, with the exception of the knife, can be made of plastic and be disposable and supplied in a sterilized form in a sealed package.

We claim:

1. A combined dilator-urethrotome, comprising:
   radially-expandable probe means comprising first and second rods, said first and second rods each having a semicircular cross section so that when said first and second rods are positioned adjacent each other, said probe means has a circular cross section;
   said first rod having a proximal end, a distal end, and a longitudinal slot cut down to a portion of its thickness, essentially from said proximal end to said distal end, said proximal end having a post member which is rigidly connected to said proximal end and is arranged at an angle to the direction of said probe means, said post having a central opening extending at said angle to the direction of said probe means;
   said second rod having a proximal end and a distal end;
   a core member rigidly connected to said proximal end of said second rod and slidingly passing through said central opening, said core member having a portion protruding outwardly from said post member, said core member having a through slot that is aligned and coincides with said slot of said first rod, said post member having a smooth cylindrical portion and a threaded portion with a male thread on its end opposite said probe means;
   said core member having on its end opposite said probe means a portion of reduced diameter so that a shoulder is formed at the point of connection of said portion of reduced diameter to the remaining part of said core;
   a cup-shaped cylindrical handle member having an edge at its open end, a closed end on the side opposite said open end, and a female thread screwed onto said male thread of said post member, said handle member having an opening in said closed end, said portion of reduced diameter of said core member extending outwardly from said closed end through said opening so that said closed end rests on said shoulder;
   locking means attached to said portion of a reduced diameter of said core member and a gap being left between said locking means and said closed end to allow rotation of said cup-shaped handle member; and
   a knife member slidingly insertable into said slot of said first rod from said proximal end of said first rod through said slot in said core member so that said knife can reciprocate within said slot of said first rod, said knife having distal and proximal ends, said distal end of said knife having a cutting blade and said proximal end of said knife having a handle.

2. The combined dilator-urethrotome of claim 1, further including auxiliary guide means in the form of a projection at the distal end of one of said first and second rods and a mating guide slot on the distal end of the other of said first and second rods, said projection and said mating guide slot having lengths that ensure engagement of said projection with said mating guide slot, even in the position of maximum dilation of said probe means, said projection and said mating guide slot having the same angle of inclination as said angle formed by said post member to said longitudinal direction of said probe means.

3. The combined dilator-urethrotome of claim 1, further Including:

a longitudinal slot cut down in said second rod to a portion of its thickness and essentially from said proximal end to said distal end of said second rod, said longitudinal slot of said first rod and said longitudinal slot of said second rod each having a cross-section consisting of a narrow guide portion and a locking portion of a larger cross section than said narrow guide portion;

said knife member having a cross section comprising a narrow guide portion and a locking portion of a larger cross section than said guide portion, said locking portion of said knife member being insertable into said locking portion of said longitudinal slot of said first rod through said proximal end of said probe means, so that said knife member can be guided along said first rod but is locked, via engagement of said locking portion of said knife member with said locking portion of said longitudinal slot, against movement in the direction perpendicular to the direction of said probe means.

4. The combined dilator-urethrotome of claim 3, further including:

a first diameter-expanding pad insertable into said longitudinal slot of said first rod when said knife member is not present in said longitudinal slot, said first diameter-expanding pad having a semicylindrical outer surface, and a portion on an inner surface of said first diameter-expanding pad having a cross section comprising a narrow guide portion and a locking portion of a larger cross section than said guide portion;

said longitudinal slot of said first rod having on said distal end of said first rod a window which is wider than said longitudinal slot of said first rod;

said longitudinal slot of said second rod having on said distal end of said second rod a window which is wider than said longitudinal slot of said second rod;

said locking portion of said first diameter-expanding pad being insertable into said locking portion of said longitudinal slot of said first rod through said window of said first rod when said knife member is not present in said longitudinal slot of said first rod, so that said first diameter-expanding pad can be guided along said first rod but is locked, via engagement of said locking portion of said first diameter-expanding pad with said locking portion of said longitudinal slot of said first rod, against movement in the direction perpendicular to said direction of said probe means; and a second diameter-expanding pad, having a semicylindrical outer surface that corresponds to the outer surface of said second rod, and a portion on the inner surface of said second diameter-expanding pad having a cross section comprising a narrow guide portion and a locking portion of a larger cross section than said guide portion, said locking portion of said second diameter-expanding pad being insertable into said locking portion of said longitudinal slot of said second rod through said window of said second rod, so that said second diameter-expanding pad can be guided along said second rod but is locked, via engagement of said locking portion of said second diameter-expanding pad with said locking portion of said longitudinal slot of said second rod, against movement in the direction perpendicular to said direction of said probe means, when said first and said second rods being positioned adjacent each, said first and second diameter-expanding pads forming a circular cross section.

5. The combined dilator-urethrotome of claim 1, further including means for measuring a degree of dilation, said means comprising a scale formed on the surface of said post member which may be read with respect to said edge of said open end of said handle member.

6. The combined dilator-urethrotome of claim 1 wherein said angle of said post member to the direction of said probe means is within the range of 90° to 135°.

7. A combined dilator-urethrotome comprising:

a radially-expandable probe comprising first and a second rods, said first and said second rods each having a semicircular cross section so that, when said first and second rods are positioned adjacent each other, said probe has a circular cross section;

said first rod having a proximal end, a distal end, and a longitudinal slot cut down to a portion of its thickness, essentially from said proximal end to said distal end, said proximal end having a post member which is rigidly connected to said proximal end of said first rod and is arranged at an angle to the direction of said probe, said post having a central opening extending at said angle to the direction of said probe;

said second rod having a proximal end, a distal end, and a longitudinal slot cut down in said second rod to a portion of its thickness and essentially from said proximal end to said distal end of said second rod, said longitudinal slot of said first rod and said longitudinal slot of said second rod each having a cross-section consisting of a narrow guide portion and a locking portion of a larger cross section than said guide portion;

a knife slidingly insertable into said longitudinal slot of said first rod, said knife having a cross section comprising a narrow guide portion and a locking portion of a locking cross section than said guide portion, said larger portion of said knife being insertable into said locking portion of said longitudinal slot through said proximal end of said probe so that said knife can be guided along said first rod but is locked, via engagement of said locking portion of said knife with said locking portion of said longitudinal slot in the first rod, against movement in the direction perpendicular to said direction of said probe;

said longitudinal slot of said second rod having on said distal end of said second rod a window which is wider than said longitudinal slot of said second rod;

a core member rigidly connected to said proximal end of said second rod and slidingly passing through said central opening, said core member having a portion protruding outwardly from said post member, said core member having a through slot that is aligned and coincides with said slot of said first rod, said post member having a smooth cylindrical portion and a threaded portion with a male thread on its end opposite said probe;

said core member having at its end opposite said probe a portion of a reduced diameter so that a shoulder is formed at the point of connection of said portion of reduced diameter to said core member;

a cup-shaped cylindrical handle member having an edge at its open end, closed end on the side opposite said open end, and a female thread screwed onto said male thread of said post member, said handle member having an opening in said closed end, said portion of a reduced diameter extending outwardly from said closed end through said opening so that said closed end rests on said shoulder;

locking means attached to said portion of a reduced diameter, a gap being left between said locking means and said closed end to allow rotation of said cup-shaped handle member;

means for measuring a degree of dilation, said means comprising a scale on the surface of said post member which may be read with respect to said edge of said open end of said handle member.

8. The combined dilator-urethrotome of claim 7, further including auxiliary guide means in the form of a projection at the distal end of one of said first and second rods and a mating guide slot on the distal end of the other of said first and second rods, said projection and said mating guide slot having lengths that ensure engagement of said projection with said mating guide slot even in the position of maximum dilation of said probe, said projection and said mating guide slot having the same angle of inclination as said angle formed by said post member to said longitudinal direction of said probe.

9. The combined dilator-urethrotome of claim 8, wherein said angle of said post member to the direction of said probe means is within the range of 90° to 135°.

10. The combined dilator-urethrotome of claim 7, further including:

a first diameter-expanding pad, having a semicylindrical outer surface that corresponds to the outer surface of said first rod, and a portion on the inner surface of said first diameter-expanding pad having a cross section comprising a narrow guide portion and a locking portion of a locking cross section than said guide portion, said larger portion being insertable into said locking portion of said longitudinal slot of said first rod through said window of said first rod, so that said first diameter-expanding pad can be guided along said first rod but is locked, via engagement of said locking portion of said first diameter-expanding pad with said locking portion of said longitudinal slot of said first rod, against movement in the direction perpendicular to said direction of said probe; and a second diameter-expanding pad, having a semicylindrical outer surface that corresponds to the outer surface of said second rod, and a portion on the inner surface of said second diameter-expanding pad having a cross section comprising a narrow guide portion and a locking portion of a locking cross section than said guide portion, said larger portion of said second diameter-expanding pad being insertable into said locking portion of said longitudinal slot of said second rod through said window of said second rod, so that said second diameter-expanding pad can be guided along said second rod but is locked, via engagement of said locking portion of said second diameter-expanding pad with said locking portion of said longitudinal slot of said second rod against movement in the direction perpendicular to said direction of said probe, in a closed position of said probe said first and second diameter-expanding pads forming in a cross section of said probe a complete circle.

* * * * *